United States Patent [19]

Hirschfeld et al.

[11] 4,123,236
[45] Oct. 31, 1978

[54] GAS CHROMATOGRAPH DEVICE

[75] Inventors: T. Hirschfeld, Framingham; David C.A.G. Brown, Cambridge, both of Mass.

[73] Assignee: Block Engineering Inc., Cambridge, Mass.

[21] Appl. No.: 553,989

[22] Filed: Feb. 28, 1975

[51] Int. Cl.² ............................................. B01D 15/08
[52] U.S. Cl. ........................................ 55/197; 55/386; 73/23.1
[58] Field of Search .......................... 55/67, 197, 386; 23/232 C; 73/23.1

[56] References Cited

U.S. PATENT DOCUMENTS

| | | | |
|---|---|---|---|
| 3,225,521 | 12/1965 | Burow | 55/197 |
| 3,364,659 | 1/1968 | Pierrard et al. | 55/197 |
| 3,374,660 | 3/1968 | McKinner et al. | 23/232 C |
| 3,405,551 | 10/1968 | Halasz | 73/23.1 |
| 3,879,984 | 4/1975 | Welland | 73/23.1 |

*Primary Examiner*—John Adee
*Attorney, Agent, or Firm*—Robert L. Slater, Jr.

[57] ABSTRACT

An improved high resolution chromatograph device operable at column pressures ranging between one and fifty atmospheres absolute measured at the column exit, means for closely regulating the column carrier gas velocity including intermittent stop flow operation, and sample collection chamber means to facilitate contamination free handling and concentration of collected pure sample during spectral or other analysis of eluted samples. Velocity and stop flow control without loss of chromatographic resolution permits matching operation time of chromatograph to that of spectral or other analysis devices.

4 Claims, 3 Drawing Figures

GAS CHROMATOGRAPH DEVICE

BACKGROUND OF THE INVENTION

1. Field of the Invention

The present invention relates in general to gas separation devices of the gas chromatographic variety and in particular, relates to improved devices for conducting gas chromatographic separation of components of volatile sample mixtures, utilizing elevated column pressure, controlled column flow rate including intermittent stop flow operation and improved means for contamination free handling and concentration of trace quantities of separated sample components.

2. Description or Prior Art

Gas chromatograph instruments comprise a class of extremely sensitive devices for the separation of components for a volatile sample mixture. Usual practice has been to mix the volatile sample with an inert carrier gas, the mixture of which is then percolated through a column containing granulated particles providing a large surface area. Depending upon the choice of the granulated packing material, a solid or liquid stationary phase is interfaced with the mobil carrier and sample mixture gaseous phase. The sample mixture components are, in the percolating process, partitioned between the mobil gaseous phase and the stationary liquid or solid phase. Each component or, if poorly resolved by the process, each class of component compounds will exhibit a unique rate of travel through a given column referred to as the retention time for the compound in the column.

Heretofore, extensive investigative work has been conducted with temperature programming of chromatographic columns and with various packing materials for columns with a purpose to increase solubility of the sample mixture in one or both the stationary phase and mobil gaseous phase. Comparable investigation work has not been conducted to date to examine the effect of increased low and intermedial range column exit pressure, i.e., gauge pressures in the range of zero to fifty atmospheres on the efficiency and operation of chromatograph columns. Some earlier work at high pressures, i.e., pressures in the 1000 to 2000 atmospheres (absolute) range, has been conducted to separate large molecular weight molecules. The earlier very high pressure investigations depended upon the altered near liquid like density of the carrier gas at extreme pressures to heighten sample solubility in the gaseous phase and facilitate separation of high molecular weight compounds. From the aforesaid high pressure investigations no readily useable laboratory device for chromatographic procedures in the pressure range of one to 50 atmospheres absolute was disclosed.

Usual practice has been to operate conventional gas chromatographs at the column gas velocity which optimizes the resolution and speed of operation for a specific sample mixture. This procedure has been achieved by operating the output opening of the column at atmospheric pressure, and regulating the flow rate of carrier gas injected into the column input opening from a pressurized tank. Commonly, the pressurized cylindrical tank reservoir of carrier gas is held at pressures above 200 atmospheres. In conventional gas chromatograph laboratory practice during operation, the pressure within the column in the vicinity of the carrier gas input opening is between one and three atmospheres gauge pressure. By adjusting the carrier gas input flow rate, the carrier gas velocity within a specific column may be adjusted to achieve the resolution and sample separation desired. The pressure drop between the input and output regions of conventional chromatograph column usage ranges between 1 and 3 atmospheres. Accordingly, the gas velocity in the column is substantial due to the pressure drop forces along the length of the column. Under these conditions, any sudden change in the gas pressure or gas velocity at the column outlet opening, such as may be induced in conventional sample collection procedures, may produce mixing within the column and reduce the resolution and separation of following separated but still entrained components.

Conventional gas chromatograph laboratory practice, in order to achieve rapid highly resolved separations, utilizes higher as distinct from lower carrier gas velocities within the column to reduce time the purified sample entrained in the lower portion of the column may be exposed to diffusion. Only with relatively high column carrier gas velocities can laminar flow through a substantial portion of the column and less mixing in the lower portions of the column in the vicinity of the column output opening be achieved under conventional column pressure ranges.

The high gas velocity in the chromatograph column causes some difficulty when the emergent separated components must be confined in a container for later analysis or use. Separated and entrained sample components within the column moving at rapid velocities "pile up" if the column is stopped or restricted in a transient manner for purposes of segregating a sample component as it leaves the column. Moreover, in chromatograph columns as conventionally operated, a pressure of approximately one atmosphere (absolute) prevails in the vicinity of the outlet opening. When the column is operated in a stop flow mode, the rate of gaseous diffusion is sufficiently high at the relatively low one atmosphere (absolute) exit pressure that the separated and entrained components of the sample mixture held in the lower portion of the column are rapidly mixed by diffusion and the resolution or separation between them is degraded. That is, a separate and pure sample component becomes contaminated with diffusion of other components of the sample from within the column.

In continuous line systems, a sample chamber, as might be utilized in spectral analysis, of separated sample components is preferably securely sealed to the output aperature of the chromatograph column. By such an arrangement, risk of contamination of a separated pure compound from outside the chromatograph column is significantly reduced. However, in such arrangement, the time for cycling the spectral analysis procedure must be coordinated with the difference in retention times of various sample components leaving the chromatograph column. Spectral analysis procedures such as Infrared Spectroscopy normally require more time than the difference in retention times of several separated compounds passing through a chromatograph column. The same condition characterizes other spectral analysis methods such as, for instance, mass spectrometry, ultra violet and visible band spectrometry, Raman spectrometry, and nuclear magnetic resonance; also a similar condition characterizes analytic procedures that are not spectral, such as electromechanical polarographic and coulometric analysis. Present laboratory practice reconciles the differences, on the one hand of the time of response of chromatographic separation processes, and on the other hand, the normally much slower response time of spectral and certain other analysis processes by one of two methods, neither of which is completely satisfactory.

First, some spectral analysis are done on the fly. The fly scan method, necessarily only one rapid scan, fails to extract the optimum spectral analysis data from the moving purified sample. Valuable data is often lost. The fly scan method, however, avoids disturbing the gas flow emitted from the column outlet opening and the attendant mixing in the gas stream due to pressure disturbance that may be reflected back into the column which stop flow operation in conventional existing devices would certainly cause.

The second method in current practice is that of storing in a detachable container a pure sample of the eluted materials issuing from the outlet of the chromatograph column. This latter approach minimizes but does not avoid the disturbance of gas flow in the column with its attendant mixing within the operating column. It may expose the pure samples to outside contamination sources. When the sample is stored, it is possible to scan repeatedly with the spectral analysis device and obtain the optimal spectral analysis data.

Conventional practice furnishes the purified sample to the storage chamber at a pressure of one atmosphere. Some spectral analysis procedures, such as infrared spectroscopy requires that the sample be concentrated before analysis, thus requiring still another step with the attendant added costs, time and contamination risks.

The most convenient manner of achieving the required time coordination between a chromatograph and a spectral analysis device is to operate the chromatograph column in a stop flow mode, provided this can be achieved without reducing the resolution and separation of subsequent entrained components.

Heretofore, no chromatograph device has been available which provided low velocity control of the carrier gas moving through the column while superior resolution of separated sample components was maintained. Similarly, heretofore, no chromatograph device has been available to this time, in which stop flow mode of operation could be conducted and good separation of eluted pure materials maintained.

Finally, an in line chamber attached to the outlet of a chromatograph column, which chamber being for the purpose of retaining sample component compounds for additional analysis, is subject to contamination by lingering traces of earlier separated samples which had previously entered the chamber from the chromatograph column. Present in line sampling equipment for continuous use, at the chromatograph output does not provide convenient or certain means for insuring that no instrumentally detectable traces of sample compounds will be retained in the spectral analysis chamber after completion of the spectral analysis operations.

OBJECTS OF THE INVENTION

It is a first object of the present invention to provide an improved general purpose gas chromatograph device in which the chromatograph column may be conveniently operated at pressures from one atmosphere to over fifty atmospheres pressures as measured at the column outlet opening.

It is another object of the present invention to provide an improved general purpose gas chromatograph device in which the velocity of the carrier gas moving through the column may be controlled and caused to move at very slow velocities without loss of separation and resolution of the purified and eluted components.

It is still another object of the present invention to provide an improved general purpose gas chromatograph suitable for direct in line operation with any of a variety of spectral analysis devices wherein the rate of emission of purified compounds from the chromatograph may be adjusted to the rate of operation of a spectral analysis device.

Still another object of the present invention is to provide an improved general purpose sensitive gas chromatograph device which facilitates stop flow operation.

Yet another object of the present invention is to provide an improved general purpose gas chromatograph device suitable for in line operation with spectral analysis devices wherein the purified compounds, emitted from the chromatograph, are not exposed to contamination from sources outside the devices nor to contamination from mixing of eluted products originating from within the devices.

And still another object of our invention is to provide an improved general purpose gas chromatograph device in which the pressure and concentration of purified sample compounds emitted from the gas chromatograph column is sufficiently high that no intermediate step to concentrate the purified samples is required prior to performing spectral analysis procedures on the samples.

These and other objects and advantages of our invention will appear from the following drawings, specification and claims.

DESCRIPTION OF PREFERRED EMBODIMENTS

Figure 1:
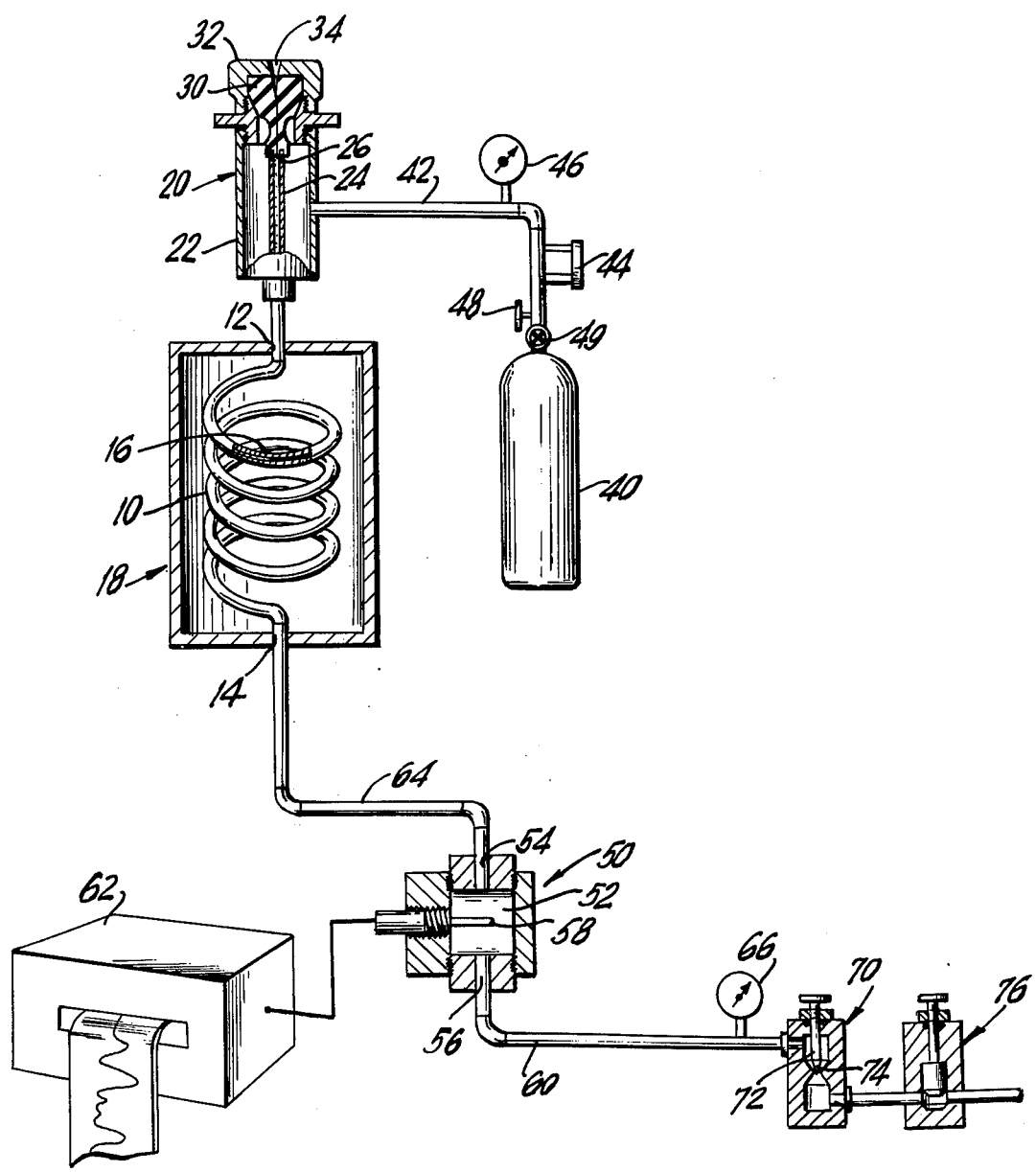
FIG. 1 shows a schematic diagram of a first preferred embodiment of our improved gas chromatograph invention.

Referring to FIG. 1, a schematic view of a first preferred embodiment of our invention is illustrated. A pressure resistant chromatograph column 10 is shown having an inlet opening 12 and an outlet opening 14. The column 10 may be packed with any of a variety of granular stationary phase materials 16, many of which are known and available to those familiar with chromatographic laboratory procedures. The column 10 is normally operated in a thermally insulated chamber or oven 18 in which the temperature of the column may be closely controlled.

An injection port 20 is mounted to the column inlet opening 12. The injection port is comprised of a heavily walled chamber 22 which may be heated from an external source not shown in the illustration to adjust the carrier gas temperature before introducing it into the column 10. An inner chamber 24 is mounted within the heavily walled chamber 22. The outlet end of the inner chamber 24 is connected to the inlet opening 12 of the column 10. The inner chamber 24 is provided near its upper end with a plurality of small apertures 26 which communicate between the interior of heavily walled chamber 22 and the interior of the inner chamber 24 through which carrier gas may be caused to flow through the inner chamber and be introduced through the inlet opening 12 into the column 10.

The upper end of the inner chamber 24 is sealed with a septum 30. The septum is a self-sealing body, through which small samples of gaseous or readily volatized mixtures may be injected into the system for elution or separation. The septum 30 is firmly sealed in place with a threaded cover 32. An aperture 34 is provided in the septum seal cover 32 through which analysis samples may be inserted.

The carrier gas is conveniently retained at relatively high pressure in a cylindrical tank reservoir 40. Pressures in commercially available cylinders of compressed gases such as purified nitrogen, carbon dioxide, helium, argon and other commonly used chromatograph carrier gases is normally available up to 200 atmospheres. The carrier gas reservoir 40 is connected through pressure resistant tubing 42 to the interior of the injection port heavily walled chamber 22. A flow rate meter 44 and a pressure gauge 46 is connected to the pressure line 42. An adjustable flow regulation valve 48 controls the quantity of carrier gas passed into the injection port and into the chromatograph column. A pressure reduction valve 49 reduces the pressure of the carrier gas to a predetermined value as it is passed into line 42.

A thermal conductivity detector 50 having a temperature controlled chamber 52, input and output openings 54 and 56 respectively, and an electronic sensing means 58. A thermistor connected through an appropriate circuit, not shown in the illustration, will sensitively detect any change in thermal conductivity of the gas present in the chamber 52. Conversely stated, the detector will detect a change in composition of gas flowing through the detector chamber 52 due to different thermal conductivity of the varied gas composition. The sensor output voltage may be displayed graphically in a moving chart recorder 62. The input opening 54 of the detector is connected through a pressure resistant line 64 to outlet opening 14 of column.

An adjustable flow restrictive valve 70 is connected on the first or inlet side to the output opening 56 of the detector through a pressure resistant line 60 and connected on the second or outlet side to a stop valve 76. The stop valve is vented to atmospheric pressure. The flow restrictive valve 70 may be a conventional pressure resistant needle valve comprised of an axially movable needle valve stem 72 which seats onto a beveled valve seat 74. The flow of gases through the flow restrictive valve may be adjusted to create any desired pressure in the vicinity of the column outlet opening greater than atmospheric pressure up to the upper pressure limits of the system. A pressure meter 66 connected to line 64 provides information of pressure at the column outlet 14. There is substantial resistance to gas flowing through the column between the inlet 12 and the outlet 14. However, there is normally negligible resistance to gas flow between the column outlet 14 and the flow restrictive valve 70, therefore, the pressure within the system measured at the gauge 66 adjacent to the flow restrictive valve 70, will be representative of the pressure within the column at the outlet opening 14.

Our invention achieves to a significant extent, the improved advantages described above such as higher resolution and stop flow operation without loss of resolution for some volatile sample mixtures at column exit pressures as low as 45 psi absolute. Some volatile sample mixture are more difficult to separate and require a larger concentrated sample for later spectral analysis. Column exit pressures of 50 atmospheres absolute and higher may be required. The embodiments described in the drawings have been constructed to operate safely at up to 50 atmospheres absolute column exit pressures. Operation at higher than 50 atmospheres absolute pressure provided the carrier gas remains in the gaseous state would not be inconsistent with the intent and purpose of our invention.

Referring to the embodiment of our invention illustrated in FIG. 1, typical operation of our invention is as follows: carrier gas is caused to flow through the injection port 20 at a preselected pressure, as shown on gauge 46, ranging between one atmosphere and fifty. The pressure reduction valve 49 readily permits the operator to establish a steady state pressure in the carrier gas flowing through pressure line 42. Any pressure, less than that present in the carrier gas reservoir tank 40, may be used. The quantity of carrier gas flowing in line 42 may be adjusted by flow control valve 48 and measured by the flow rate meter 44.

The flow resistance valve 70 is then adjusted to fix the column exit pressure, as observed on gauge 66, to any preselected value between zero and fifty atmospheres or more. When the gauge 66 indicates zero gauge pressure, the chromatograph is being operated in the conventional manner. Our invention relates to a chromatograph capable of operation above zero column exit gauge pressure.

Velocity of flow through the column 10 and detector 50 may be regulated at column exit pressures greater than zero gauge pressure by adjustments of the flow rate valve 48. At higher column pressure, very low gas velocity within the column may be attained without loss of chromatographic resolution.

Stop flow operation is conveniently achieved by simultaneously closing the flow rate valve 48 and the vent stop valve 76. Stop flow operation without loss of resolution of the remaining entrained sample components may be readily attained if the valves 48 and 76 are closed on a slow moving rather than a rapidly moving gas flow.

Figure 2:
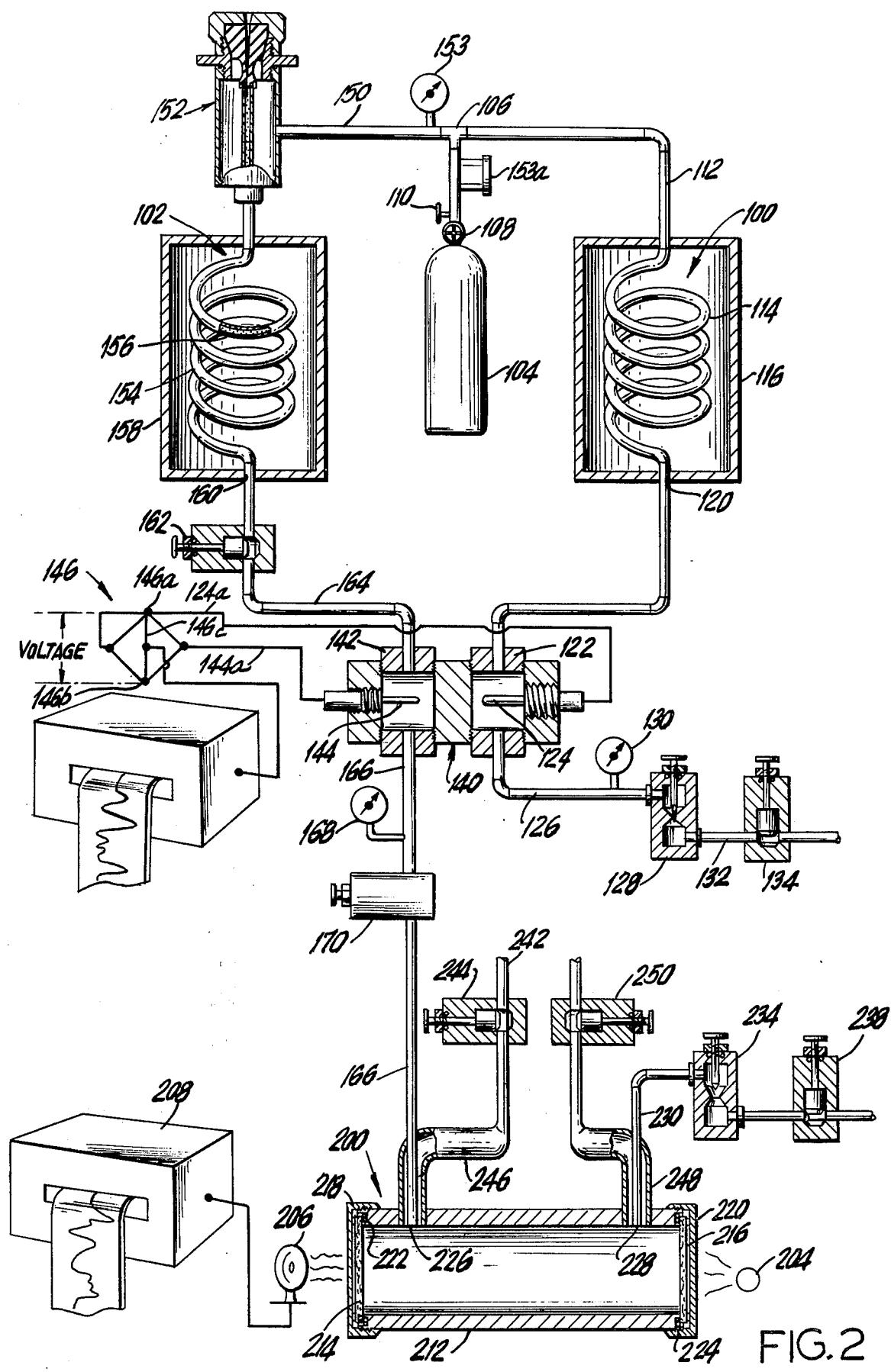
FIG. 2 shows a schematic diagram of another preferred embodiment of our invention in which our improved gas chromatograph is fixedly combined in line with a sample chamber adapted to perform infrared spectroscopy analysis.
Figure 3:
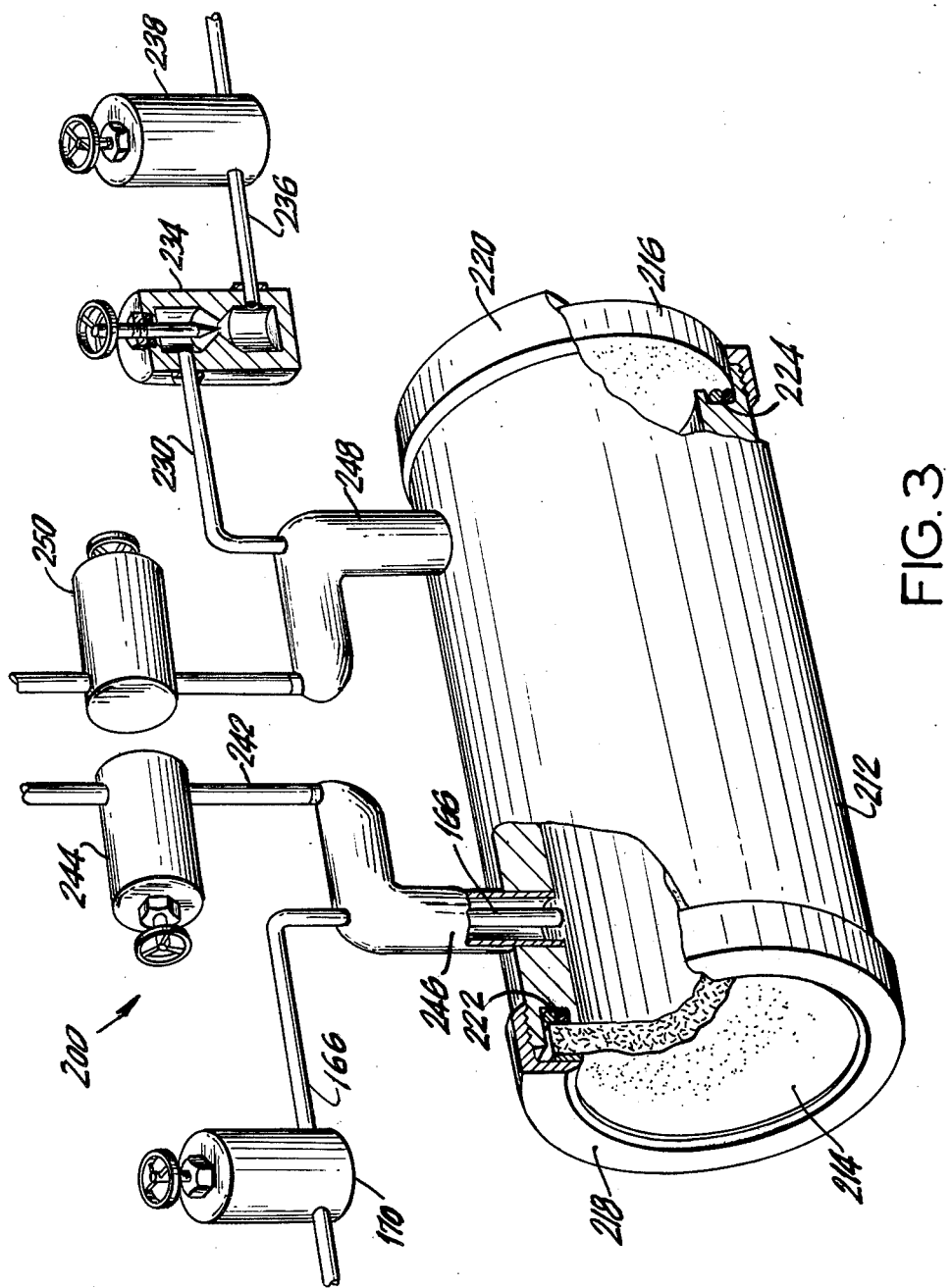
FIG. 3 shows a partially cutaway view of a sample chamber suitable for infrared spectroscopy illustrated schematically in FIG. 2 and the gas chromatograph output means of our invention connecting to the interior of the sample chamber.

Referring now to a preferred embodiment of our invention, illustrated in FIGS. 2 and 3, wherein our invention is applied to a dual column chromatograph system having a reference chromatograph 100 mounted for simultaneous operation with an analytic chromatograph 102. A pressurized reservoir of carrier gas 104 is connected through a pressure line Tee connection 106. Carrier gas is caused to flow at the desired pressure and rate, respectively, by adjustment of pressure reduction valve 108 and flow regulator valve 110 into the pressure line Tee 106. A first side of the Tee 106 is connected through a pressure line 112 to the reference chromatograph column 114. The column 114 is mounted within a thermally insulated container 116 in which the temperature of the column may be controlled within narrow limits. The outlet 120 of the reference column is connected to one side 122 of a dual channel thermal conductivity detector 140. The dual detector on side 122 has an electronic sensing element 124. Gases flowing through side 122 of the detector exit through a short line 126 which terminates in a flow restrictor means 128. The flow restrictor means 128, shown in the illustration is an adjustable needle valve. A fixed restriction which could be a diaphragm having a sized aperture, which is not shown in the illustration, could be adapted to serve the function of the needle valve, particularly as applied to the reference chromatograph. Column exit pressure may be observed on pressure gauge 130. A short line 132 connects the low pressure or exit side of the flow restrictor 128 to a stop valve 134. The stop valve 134 is vented to the atmosphere.

Referring now to the analytic chromatograph 102, the carrier gas emitted from the second side of the Tee pipe fitting 106 passes through a pressure line 150 into an injection port assembly 152. An injection port assembly, one preferred configuration of which was described in some detail in connection with the embodiment in FIG. 1, is a means wherein the carrier gas and the volatile sample is mixed and introduced into the chromatograph column 154. The reference gas chromatograph column 114 and the analytic column 154 are loaded with identical solid or solid-liquid stationary phase packing 154. The analytic column 154 is mounted in a thermally insulated container 158. The column exit or outlet 160 of the column 154 is fitted for convenience with a stop valve 162. A line 164 connects the column outlet 158 to a second side 142 of the dual detector 140. The gas emitting from the detector on the analytic side 142, passes through a line 166 into which a pressure gauge 168 and a stop valve 170 has been mounted. The line 166 terminates in a sample collection chamber shown at 200 in the drawings and described below.

The analytic column detector 142 is comprised of an electronic thermal sensor 144. The electronic sensors, 124 on the reference side and 144 on the analytic side, are two substantially identical thermistors mounted to optimally detect any variation in thermal conductivity of the respective gas streams which flow over them. Leads 124a and 144a terminate on opposing branches of an electrical bridge 146. The bridge network is powered by a voltage applied between points 146a and 146b. The bridge network is completed by connecting line 146c at the electrical center, of which, a conductor 148 connects to the recorder 149.

The recorder when connected, as described above and shown in FIG. 2, records the instantaneous difference in voltage (millivolt units) between the two detectors. Thus, base line drift of the detector, due to any of a variety of extraneous causes, can be controlled and eliminated from the record.

The sample collection chamber shown at 200 in FIGS. 2 and 3 is adapted in the present illustrative embodiment to facilitate infrared spectral analysis of purified concentrated samples emitted from the analytic chromatograph 102. An infrared spectrophotometer is shown schematically as an infrared radiation source 204, an infrared sensor or bolometer 206 and a recorder 208. The reference to infrared spectrum analysis is purely illustrative; other analytic processes may be conveniently performed using our sample collection chamber 200. Examples of alternative analytic processes are Raman spectroscopy, ultra violet and visible band spectroscopy, mass spectroscopy and nuclear magnetic resonance.

The sample collection chamber is comprised of a pressure resistant cylindrical member 212 open at each end. The ends of the cylindrical member are closed in the illustrated example with infrared transparent crystal windows 214, 216. Crystalline sodium chloride is a frequent window choice in infrared systems. The windows are sealed in place to the cylindrical member 212 with threaded retainer caps 218, 220. Pressure resistant leak proof seals 222, 224 are used to seal the windows 214, 216 to the open ends, respectively, of the cylindrical member 212.

Gases emitted from the analytic chromatograph column 154 flow through connecting line 166 and enter the interior of the chamber through a first inlet port 226. In normal operation, gases exit through outlet port 228. A short connecting line 230 connects through the sample chamber outlet port 228 to a flow restive means 234. The flow restrictive means in the embodiment, shown in the illustration, is an adjustable needle valve. The flow restrictive means 234 is connected on the exit or low pressure side through a short length of line 236 to stop valve 238. The stop valve vents to the atmosphere.

Spectral analysis methods have the capability of identifying one part in one million or more concentration in a sample. Accordingly, utmost precautions must be taken to insure no extraneous contamination is mixed in a purified sample. The eluted samples emitted from the chromatograph column 154 are mixed with and carried along with carrier gas. Carrier gas is thus a preferred fluid with which to exhaust and clean the sample chamber after each usage. To accomplish this purpose, a line 242 onto which a stop valve 244 is mounted connects with a source of pressurized carrier gas, not illustrated in the drawing. Line 242 connects to the interior of the sample chamber 200 through an inlet manifold 246. It has been convenient to pass the inlet line 166 through the inlet manifold 246 as shown in the illustrations.

An exhaust manifold 248 connects with the interior of the sample column through the outlet port 228 and vents to the atmosphere through a stop valve 250.

The exhaust manifold 248 is not critical for general usage. Exhaust of the sample chamber 200 during high pressure carrier gas flush can be readily made through the line 230 and through the flow restrictor 234 and stop valve 238. The large exhaust manifold facilitates a larger quantity of carrier gas at high velocity to pass through the sample chamber with less resistance thus achieving better evacuation of the chamber in preparation for receiving the next sample.

The sample chamber may be utilized as a stop flow collection chamber when the exit line 230 is closed with the stop valve 238 or may be used in a fly scan spectral analysis process where the exit line 230 is left open.

Samples may be concentrated at whatever pressure the operator may desire by making appropriate adjustments in the pressure reduction valve 108 and simultaneously the flow restriction means 128 and 234. The sample pressure chamber will collect selected samples with our arrangement at the pressure at which the chromatograph separation is conducted. Pressure within the sample chamber may be read on pressure gauge 168, which pressure will also be the pressure at the column exit 160.

The foregoing descriptions of the structure and operation of preferred embodiments of our invention are intended as being illustrative only; the scope of our invention is set forth below in claims.

We claim:

1. An improved gas chromatograph apparatus comprised of a pressure resistant gas chromatograph column, the column having an inlet opening at a first end and an outlet opening at a second end, an injection port means mounted to the column inlet opening, a reservoir of pressurized carrier gas, adjustable inlet pressure regulation means connecting the carrier gas reservoir to the injection port, the injection port means being provided with means for combining sample gaseous mixtures with the pressurized carrier gas and introducing these gases under pressure into the inlet opening of the column, adjustable flow restrictive means, the flow restrictive means being mounted to the column outlet opening, the flow restrictive means being adapted to adjust the pressure within the column in the vicinity of the column outlet opening from 1 atmosphere absolute upward to at least 50 atmospheres absolute pressure, whereby with appropriate adjustment of the flow restrictive means chromatograph separations of sample gas mixtures may be conducted within the column at absolute pressures measured at the column outlet opening in the range upward from one atmosphere to above 50 atmospheres absolute pressure, whereby the velocity of the gases flowing through the column may be adjusted to conform to a preselected value by simultaneously adjusting the flow restricting means at the outlet opening to fix the desired column pressure and adjusting the inlet pressure regulation means to fix the desired carrier gas column pressure, the aforesaid chromatograph apparatus further being a sample collection chamber, the sample collection chamber having an input port and an output port, the sample collection chamber input port being connected to the column outlet opening and the sample collection chamber output port being connected to the adjustable flow restriction means, a stop valve, the stop valve having a first and a second side, the first side being mounted to the flow restriction means and the second side venting to the atmosphere, whereby eluted pressurized samples of gas may be collected at low gas velocities in the sample collection chamber.

2. The gas chromatograph device with a sample collection chamber device of claim 1 wherein the sample collection chamber has a second input port and a second output port, the two input ports and the two output ports, respectively, being selectively closed and opened by means of our stop valves mounted, respectively, on each of the two input and two output ports, the second input port being connected to a supply of pressurized carrier gas, the second output port opens to the atmosphere, whereby during normal operation, the second input port and second output port valves are closed during the flushing cycle to prepare for receiving a sample into the chamber, the first input and first output valves are closed, the second ports opened and pressurized carrier gas passed through the sample chamber.

3. An improved gas chromatograph apparatus for stop flow operation comprised of a pressure resistant gas chromatograph column, the column having an inlet opening at a first end and an outlet opening at a second end, an injection port, the injection port being mounted to the column inlet opening and being provided with means for introducing under pressure a flow of carrier gas and sample gaseous mixtures into the column, a flow restrictive means, the flow restrictive means being mounted below the column outlet and being adapted to fix and maintain gas pressure within the column, so that when measured at the column outlet a pressure selected from within the range between 2 atmospheres and 50 atmospheres absolute pressure may be maintained within the column, the flow restrictive means being further adapted to regulate at the selected pressure the velocity of the gases moving through the column, a quick response first stop valve, the stop valve being mounted juxtaposed to the column outlet opening, and a sample chamber, the sample chamber being provided with an input port and an output port, a second stop valve being mounted to the chamber output port, the flow restrictive means being mounted to the second stop valve on the sample chamber output port, the sample chamber input port being mounted to the quick response stop valve, whereby separated eluted gaseous samples may be collected, concentrated under pressure and held within the sample chamber for additional analysis by intermittently opening the quick action first stop valve to connect the input port of the sample chamber to the chromatograph column, then after entraining the gaseous sample within the sample chamber closing the quick action first stop valve and the second stop valve on the sample chamber outlet port to retain the isolated gaseous sample within the chamber.

4. A gas chromatograph device with a sample collection chamber comprised of a pressure resistant gas chromatograph column, the column having an inlet opening at a first end and an outlet opening at a second end, an injection port, the injection port being mounted to the column inlet opening and being provided with means for introducing under pressure a flow of carrier gas and sample gaseous mixtures into the column, a flow restrictive means, the flow restrictive means being mounted to means in pressure connected relationship to the column outlet opening, and being adapted to sustain pressures within the column so that when measured at the column outlet a pressure selected from within the range between two atmospheres and fifty atmospheres absolute may be maintained within the column, the flow restrictive means being further adapted to regulate at the selected pressure the velocity of the gases moving through the column, a quick response first stop valve, the stop valve being mounted juxtaposed to the column outlet opening, and a sample chamber, the sample chamber being provided with a first inlet port and a first outlet port, the sample chamber first inlet port being mounted to the quick response first stop valve, the flow restrictive means being mounted to the sample chamber first outlet port, the sample chamber having a second inlet port and a second outlet port, the second inlet port and the two outlet ports, respectively, being selectively closed and opened by means of separate stop valves mounted, respectively, on the second inlet and the two outlet ports, the second inlet port being connected to a supply of pressurized carrier gas, the second outlet port through the aforesaid stop valve opening to the atmosphere, whereby separated eluted gaseous samples concentrated under pressure may be separately collected and held within the sample chamber for additional analysis by intermittently opening the quick action first stop valve to connect the inlet port of the sample chamber to the chromatograph column, then after entraining the gaseous sample chamber closing the quick action first stop valve and the remaining sample chamber valves to retain the isolated gaseous sample therein and whereby the sample chamber may be prepared to receive succeeding samples by flushing with carrier gas wherein the first input port and first output port stop valves are closed and the second input port and second output port stop valves are opened, pressurized carrier gas passed through the sample chamber, then the second inlet port and second outlet port stop valves are closed and the device is ready for normal operation.

* * * * *